(12) United States Patent
Ovadya et al.

(10) Patent No.: US 8,935,880 B2
(45) Date of Patent: Jan. 20, 2015

(54) METHODS FOR MANIPULATING YIELD OF PLANTS AND IDENTIFYING YIELD GENES

(75) Inventors: Daniel J. Ovadya, Davis, CA (US); Bala Karunanandaa, Creve Coeur, MO (US); Karen Gabbert, St. Louis, MO (US); Qin Zeng, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 721 days.

(21) Appl. No.: 13/062,507

(22) PCT Filed: Sep. 4, 2009

(86) PCT No.: PCT/US2009/055975
§ 371 (c)(1),
(2), (4) Date: May 17, 2011

(87) PCT Pub. No.: WO2010/028205
PCT Pub. Date: Mar. 11, 2010

(65) Prior Publication Data
US 2011/0207615 A1 Aug. 25, 2011

Related U.S. Application Data

(60) Provisional application No. 61/095,126, filed on Sep. 8, 2008.

(51) Int. Cl.
*A01H 3/02* (2006.01)
*A01G 7/04* (2006.01)
*A01H 5/00* (2006.01)

(52) U.S. Cl.
CPC .......................................... *A01H 3/02* (2013.01)
USPC ...... 47/58.1 LS; 435/410; 435/414; 435/415; 800/290

(58) Field of Classification Search
None
See application file for complete search history.

(56) References Cited

U.S. PATENT DOCUMENTS

2014/0259905 A1    9/2014   Ovadya et al.

OTHER PUBLICATIONS

Raper & Thomas_Crop Sci_16_667_1976.*
Thomas & Raper_Bot Gaz_138_321_1977.*
Sysoeva Markovskaya_Russ J Dev Biol_37_16_2006.*
Egli Browning_J Agronomy_24_11_2006.*
Jian_BMC Mol Biol_9_59_2008.*
Downs Thomas_Biotronics_19_19_1990.*
Han_Soybean Science_14_283_1995_abstract only in English.*
Guiament_Phyton_44_37_1984_abstract.*
Han_Acta Agron Sinica_25_349_1999_abstract only in English.*
Hamner_62 to 89_1969.*
Blaney_Bot Gaz_119_11_1957.*
Guiamet et al., "The effects of long days upon reproductive growth in soybeans (*G. max* L.) cv. Williams," *Japanese Journal of Crop Science*, 53(1):35-40, 1984.
Raper et al., "Photoperiodic alteration of dry matter partitioning and seed yield in soybeans," *Crop Science*, 18(4):654-656, 1978.
Kantolic et al., "Reproductive development and yield components in indeterminate soybean as affected by post-flowering photoperiod," *Field Crops Research*, 93(2-3):212-222, 2005.
Kantolic et al., "Development and seed number in indeterminate soybean as affected by timing and duration of exposure to long photoperiods after flowering," *Annals of Botany*, 99(5):925-933, 2007.
Han et al., "Postflowering photoperiod regulates vegetative growth and reproductive development of soybean," *Environmental and Experimental Botany*, 55(1-2):120-129, 2006.
Kantolic et al., "Photoperiod sensitivity after flowering and seed number determination in indeterminate soybean cultivars," *Field Crops Research*, 72(2):109-118, 2001.
Ellis et al., "Effects of photoperiod and maturity genes on plant growth, partitioning, radiation use efficiency, and yield in soyabean [*Glycine max* (L.) Merrill] 'Clark'," *Annals of Botany*, 85(3):335-343, 2000.
Jian et al., "Validation of internal control for gene expression study in soybean by quantitative real-time PCR," *BMC Molecular Biology*, 9(59):1-14, 2008.
U.S. Appl. No. 14/207,284, filed Mar. 12, 2014, Ovadya et al.

* cited by examiner

*Primary Examiner* — Medina A Ibrahim
*Assistant Examiner* — Russell Boggs
(74) *Attorney, Agent, or Firm* — Dentons US LLP; David Lanzotti, Esq.

(57) ABSTRACT

Methods for manipulating yield and generation time of plants, especially short day plants such as soybean are provided. The methods comprise manipulating external signals such as long day conditions, short day conditions, growth medium, and nutrient supply.

24 Claims, No Drawings

METHODS FOR MANIPULATING YIELD OF PLANTS AND IDENTIFYING YIELD GENES

CROSS REFERENCE TO RELATED APPLICATIONS

This application claims priority to U.S. Provisional Patent Application Ser. No. 61/095,126, filed Sep. 8, 2008, which is hereby incorporated by reference herein in its entirety.

FIELD

The present invention discloses methods for manipulating yield of plants and identifying yield genes. More specifically, the present invention discloses methods for manipulating seed yield of short day plants such as soybean plants and identifying yield genes from soybean plants.

BACKGROUND

Plant growers are always looking for new methods for manipulating yield of a plant, especially for enhancing seed yield of an economically important plant such as soybean. Further, manipulation of seed yield or seed production time is useful in advancing a seed quickly through the product development phases such as through growth chamber, nursery, green house, and field testing.

Applicants have been able to manipulate the yield of a short day plant such as soybean plant by manipulating its vegetative and flowering responses with external signals such as exposure to long day growing conditions, exposure to short day growing conditions, growth medium, and nutrient supply. Further, the method can be used for identifying yield genes involved in such as genes involved in early induction of flowering, pod set, and retention and/or abscission of flowers and pods.

SUMMARY

A method for manipulating yield of a short day plant is provided. The method includes a step of initiating growth of at least one short day plant under long day growing conditions. The short day plant is selected from the group consisting of soybean, cotton, rice, sugarcane, tobacco, and strawberry. The long day growing conditions comprise at least about 14 hours of light per day at a light intensity of from about 1000 to about 2000 µmoles $m^{-1}s^{-1}$ and a temperature of from about 84° F. to about 90° F. and a night temperature of from about 62° F. to about 70° F.

The method further comprises controlling the environment of the short day plant to provide for short day growing conditions for about 3 to about 21 days. The period of short day growing conditions is initiated at a plant growth stage of from about V1 to about V4. The short day growing conditions comprise maintaining about 9 to about 11 hours of light per day at light intensity of about 700 to about 900 µmoles µmoles $m^{-1}s^{-1}$ and a temperature of from about 78° F. to about 82° F. and about 14 hours of night at a temperature of from about 66° F. to about 70° F.

The method further comprises returning the plant to long day growing conditions. As described above, the long day growing conditions comprise at least about 14 hours of light per day at a light intensity of from about 1000 to about 2000 µmoles $m^{-1}s^{-1}$ and a temperature of from about 84° F. to about 90° F. and a night temperature of from about 62° F. to about 70° F.

In another embodiment, the method of the present invention further comprises growing the short day plant under conditions that restricts vegetative growth and enhances flowering. Such conditions comprise growing the short day plant in a soil volume of about 2.0 mL to about 4.0 mL per seed to be produced.

In another embodiment, the method of the present invention further comprises providing the short day plant nutrients sufficient to support seed development. Such nutrients may be selected from the group consisting of Calcium Nitrate, Phosphate, micronutrients, and Magnesium Sulfate wherein the amount of nutrients supplied provides a soil EC of from about 1.0 to about 1.6 mmhos and a soil pH of from about 5.1 to about 6.0.

A method for manipulating yield of a soybean plant is also provided. The method comprises initiating growth of at least one soybean plant under long day growing conditions. The long day growing conditions comprise at least about 14 hours of light per day at a light intensity of about 1000 to about 2000 µmoles $m^{-1}s^{-1}$ and a temperature of from about 84° F. to 90° F. and a night temperature of from about 62° F. to about 70° F.

The method further comprises controlling the environment of the soybean plant to provide for short day growing conditions for about 3 to about 21 days. The period of short day growing conditions is initiated at a plant growth stage of from about V1 to about V4. The short day growing conditions comprise maintaining about 9 to about 11 hours of light per day at a light intensity of from about 700 to about 900 µmoles m–1s–1 and a temperature of from about 78° F. to about 82° F. and about 14 hours of night at a temperature of from about 66° F. to about 70° F.

The method further comprises returning the plant to long day growing conditions. As described above, the long day growing conditions comprise at least about 14 hours of light per day at a light intensity of from about 1000 to about 2000 µmoles $m^{-1}s^{-1}$ and a temperature of from about 84° F. to 90° F. and a night temperature of from about 62° F. to about 70° F.

In another embodiment, the method of the present invention further comprises growing the soybean plant under conditions that restricts vegetative growth and enhances flowering. Such conditions comprise growing the soybean plant in a soil volume of from about 2.0 mL to about 4.0 mL for every seed to be produced.

In yet another embodiment, the method of the present invention further comprises providing the soybean plant nutrients sufficient to support seed development. Such nutrients may be selected from the group consisting of Calcium Nitrate, Phosphate, micronutrients, and Magnesium Sulfate wherein the amount of nutrients supplied provides a soil EC of from about 1.0 to about 1.6 mmhos and a soil pH of from about 5.1 to about 6.0.

Still further, another embodiment of the invention comprises methods for identifying genes conferring increased yield in a short day plant. The methods generally comprise initiating growth of at least one short day plant under long day growing conditions and controlling the environment of the at least one short day plant to provide for short day growing conditions for about 3 to about 21 days. The at least one short day plant is then returned to long day growing conditions and tissue is harvested from the at least one short day plant. Transcriptional profiling is then performed on the harvested tissue to identify potential genes that may confer increased yield in the at least one short day plant.

DETAILED DESCRIPTION

Unless defined otherwise, all technical and scientific terms used herein have the same meaning as commonly understood by one of ordinary skill in the art to which this invention belongs. Generally, the nomenclature used herein and the manufacture or laboratory procedures described below are well known and commonly employed in the art. Conventional methods are used for these procedures, such as those provided in the art and various general references. Where a term is provided in the singular, the inventors also contemplate aspects of the invention described by the plural of that term. Where there are discrepancies in terms and definitions used in references that are incorporated by reference, the terms used in this application shall have the definitions given herein. The inventors do not intend to be limited to a mechanism or mode of action. Reference thereto is provided for illustrative purposes only.

The present description discloses methods for manipulating seed yield per plant. In one embodiment, it is the seed yield of a short day plant. In another embodiment, it is the seed yield of a soybean plant. The present description also discloses methods for reducing the seed generation time of a plant. In one embodiment, it is the seed generation time of a short day plant. In another embodiment, it is the seed generation time of a soybean plant.

The methods described herein comprise the manipulation of external vegetative and reproductive signals to control seed production. For example, by using the instant methods, a soybean plant can be manipulated to produce a specific amount of seeds in a required time for a specific project. For example, as described in Table 2 below, a soybean plant can be manipulated to produce 4000 seeds in 170 days or 90 seeds in 80 days as compared to 200 seeds in 120 days under normal growing conditions represented by the control method (see Table 2). The methods described herein solve a wide range of seed production needs required during research, regulatory, breeding, and commercial phases of product development. For example, the amount of seeds produced and the amount of time required to produce such seeds can be varied depending on the need in a particular product development phase.

In a particular application of the methods of the present invention, increasing the amount of seeds produced from a single plant can reduce the amount of work required for molecular characterization of pure seeds for commercial production. For example, 12-18 sibling lines are traditionally bulked to create a commercial seed lot with confirmed genetic purity. However, using the methods described herein, Applicants have demonstrated that only one or two plants are needed to produce a commercial seed lot, thus significantly reducing the amount of quality assurance and/or quality control assays required on the sibling lines.

Increasing the amount of seeds produced from a single plant may also be beneficial so that archiving, biochemical analyses e.g., oil and fatty acid analyses, and germination studies can be completed using seeds from a single plant thus reducing the variation in source material when more than one plant is used.

Further benefits of the present invention can be achieved by producing more developing pods from a single plant. More developing pods provides for more immature embryos which in turn can supply the relatively large amounts of protein normally required for conducting studies for regulatory dossier.

Producing more seeds from a single plant may further enables the identification of more progeny seeds with an acceptable molecular profile, e.g., seeds with single copy inserts without the vector backbone expressing a gene of interest at an efficacious level, from plants transformed with 2T constructs or multiple-traits where the probability of finding a desired seed is lower in a population of seeds. For example, only 1 out of 256 seeds is likely to contain a triple homozygous marker-free plant. With a large number of seeds produced from a single plant, it is easier to identify such a seed.

The methods described herein may further reduce generation time which can enable rapid advancement of a seed to meet specific field planting deadlines, obtain acceptable molecular profiles and sufficient seed yields, and provide improved efficiency of large grow-outs due to high plant density.

Further, the methods of the present invention may eliminate the need for Short Day Greenhouses as these are difficult to cool in summer. The warm, dark conditions encountered in the summer during night in a Short Day Greenhouse cause flower abortion and excessive night respiration stress. These Greenhouses are expensive to build and older greenhouse may be difficult to retrofit.

Without being held to a particular theory, experience to date suggests that the methods described herein appear to disrupt, enhance, or compete with a plant's normal circadian rhythm to trigger early flowering on physiologically young plants. Thus, Applicants believe that the method may enhance yield by inducing indeterminate flowering, more branching, shorter internodes, and more flowers and pod set per internode.

The methods of the present invention allow a grower to customize the seed yield and generation time to meet specific business needs. The per plant yields can be increased by up to 30 fold (from 200 seeds to 6000 seeds) or the generation time can be decreased by 30% (250 seeds in 90 days vs. 120 days).

The methods can also be performed year round and could eliminate the need for winter nurseries thus increasing the throughput of the product development process and reducing the total time needed to test a particular seed for developing the commercial seed. Producing more seeds enables conducting field trials in a single location several months faster than the seeds produced with the current Short Day methods. Current short day methods require an extra seed increase generation step in the field to obtain sufficient seeds for conducting a field trial in one location in a subsequent year. The time savings of several months could lead to earlier commercial launch dates and ultimately additional product revenues.

A method for manipulating yield of a short day plant is provided. The method comprises initiating growth of at least one short day plant under long day growing conditions. The short plant is selected from the group consisting of soybean, cotton, rice, sugarcane, tobacco, and strawberry. In one embodiment, the long day growing conditions comprise at least about 14 hours of light per day at a light intensity of from about 1000 to about 2000 µmoles $m^{-1} s^{-1}$ and a temperature of from about 84° F. to about 90° F. and a night temperature of from about 62° F. to about 70° F. In another embodiment, the long day growing conditions comprise about 18 hours of light per day at a light intensity of about 2000 µmoles $m^{-1} s^{-1}$ and a temperature of about 86° F. and a night temperature of about 68° F.

The method further comprises controlling the environment of the short day plant to provide for short day growing conditions for about 3 to about 21 days. The period of short day growing conditions is initiated at a plant growth stage of from about V1 to about V4. In one embodiment, the short day growing conditions comprise maintaining from about 9 to about 11 hours of light per day at a light intensity of from about 700 to about 900 µmoles µmoles $m^{-1} s^{-1}$ and a temperature of from about 78° F. to about 82° F. and about 14 hours of night at a temperature of from about 66° F. to about 70° F. In another embodiment, the short day growing conditions comprise maintaining about 10 hours of light per day at a light intensity of about 900 μmoles m$^{-1}$ s$^{-1}$ and a temperature of about 80° F. and about 14 hours of night at a temperature of about 68° F.

The method further comprises returning the plant to long day growing conditions. As described above, in one embodiment, the long day growing conditions comprise at least about 14 hours of light per day at a light intensity of from about 1000 to about 2000 μmoles m$^{-1}$s$^{-1}$ and a temperature of from about 84° F. to about 90° F. and a night temperature of from about 62° F. to about 70° F. In another embodiment, the long day growing conditions comprise about 18 hours of light per day at a light intensity of about 2000 μmoles m$^{-1}$ s$^{-1}$ and a temperature of about 86° F. and a night temperature of about 68° F. In current green house methods and field production methods plants are typically allowed to grow under short day or under decreasing day light conditions until seeds are harvested. Without being held to a particular theory, Applicants believe that returning the plant to long day growing conditions may send a vegetative signal to already reproductive plants, providing up to 800 more hours of photosynthesis than the current greenhouse method and resulting in increased branching, shorter internodes, and more pods per internode. Longer photoperiods also allow the night temperature to be reduced, which results in very high self-pollination rates and pod set compared to the current greenhouse method where higher night temperatures can lead to a higher rate of flower abortion and lower pod set. In addition to providing a constant long day photoperiod, the instant methods may include a gradually increased long day photoperiod from about 16 hours to about 20 hours over a period of 3 weeks. Gradually increasing long day photoperiods may send an additional long day signal to the plant thereby creating plants with very high average seed yields of about 2000 to about 4000 seeds.

In alternative embodiments, the methods of the present invention may further comprise growing the short day plant under conditions that restrict vegetative growth and enhance flowering. Such conditions may include growing the short day plant in a soil volume of from about 2.0 mL to about 4.0 mL for every seed to be produced. This can be achieved by controlling pot size. Different pot sizes can be used to increase or decrease the flowering response. Generally, smaller pot size will reduce vegetative growth and increase the flowering response leading to very determinate growth habit and larger pot size will increase vegetative growth and allow for indeterminate flowering, more pods, and more seeds.

In still other embodiments, the methods of the present invention may further comprise providing the short day plant with nutrients sufficient to support seed development. In one embodiment, such nutrients can be selected from the group consisting of Calcium Nitrate, Phosphate, micronutrients, and Magnesium Sulfate. In another embodiment, the nutrients are supplied in amounts sufficient to provide a soil EC of about 1.0 to about 1.6 mmhos and a soil pH of from about 5.1 to about 6.0. The nutrients can be provided by utilizing advanced irrigation techniques such as soil-less media, continuous liquid fertilization, and optimal moisture management. Applicants have discovered that under these conditions, the plants become root-bound, contributing to the vegetative and flowering signals needed for enhanced yield. Under root-bound conditions, the plants still require complete mineral nutrition and moisture. This is achieved by administering fertilizer solutions several times to each pot.

A method for manipulating yield of a soybean plant is also provided. The method comprises initiating growth of at least one soybean plant under long day growing conditions. In one embodiment, the long day growing conditions comprise at least about 14 hours of light per day at a light intensity of from about 1000 to about 2000 μmoles m$^{-1}$s$^{-1}$ and a temperature of from about 84° F. to 90° F. and a night temperature of from about 62° F. to about 70° F. In another embodiment, the long day growing conditions comprise about 18 hours of light per day at a light intensity of about 2000 μmoles m$^{-1}$ s$^{-1}$ and a temperature of about 86° F. and a night temperature of about 68° F.

The method further comprises controlling the environment of the soybean plant to provide for short day growing conditions for about 3 to about 21 days. The period of short day growing conditions is initiated at a plant growth stage of from about V1 to about V4. In one embodiment, the short day growing conditions comprise maintaining about 9 to about 11 hours of light per day at a light intensity of from about 700 to about 900 μmoles μmoles m$^{-1}$ s$^{-1}$ and a temperature of from about 78° F. to about 82° F. and about 14 hours of night at a temperature of from about 66° F. to about 70° F. In another embodiment, the short day growing conditions comprise maintaining about 10 hours of light per day at a light intensity of about 900 μmoles m$^{-1}$ s$^{-1}$ and a temperature of about 80° F. and 14 hours of night at a temperature of about 68° F.

The method further comprises returning the plant to long day growing conditions as described above.

In another embodiment, the method of the present invention further comprises growing the soybean plant under conditions that restrict vegetative growth and enhance flowering. Such conditions may include growing the soybean plant in a soil volume of from about 2.0 mL to about 4.0 mL for every seed to be produced. This can be achieved by controlling pot size. Different pot sizes can be used to increase or decrease the flowering response. Generally, smaller pot size will reduce vegetative growth and increase the flowering response leading to very determinate growth habit and larger pot size will increase vegetative growth and allow for indeterminate flowering, more pods, and more seeds.

In yet another embodiment, the method of the present invention further comprises providing the soybean plant with nutrients sufficient to support seed development. In one embodiment, such nutrients can be selected from the group consisting of Calcium Nitrate, Phosphate, micronutrients, and Magnesium Sulfate. In another embodiment, the nutrients are supplied in an amount sufficient to provide a soil EC of about 1.0 to about 1.6 mmhos and a soil pH of about 5.1 to about 6.0. The nutrients can be provided by utilizing advanced irrigation techniques such as soil-less media, continuous liquid fertilization, and optimal moisture management. Applicants have discovered that under these conditions, the plants become root-bound, contributing to the vegetative and flowering signals needed for enhanced yield. Under root-bound conditions, the plants still require complete mineral nutrition and moisture. This is achieved by administering fertilizer solutions several times to each pot.

A method for identifying yield genes from a short day plant is provided. The method comprises: initiating growth of at least one short day plant under long day growing conditions; controlling the environment of the at least one short day plant to provide for short day growing conditions for about 3 to about 21 days; returning the plant to long day growing conditions; and performing transcriptional profiling from a tissue harvested from the plant grown in step b) and c) to identify yield genes.

The short day plant is selected from the group consisting of soybean, cotton, rice, sugarcane, tobacco, and strawberry. In one embodiment the short day plant is a soybean plant.

The long day growing conditions comprise at least about 14 hours of light per day at a light intensity of from about 1000 to about 2000 μmoles m$^{-1}$s$^{-1}$ and a temperature of from about 84° F. to about 90° F. and a night temperature of from about 62° F. to about 70° F.

The method further comprises the step of controlling the environment of the short day plant to provide for short day growing conditions for about 3 to about 21 days. The period of short day growing conditions is initiated at a plant growth stage of from about V1 to about V4. The short day growing conditions comprise maintaining about 9 to about 11 hours of light per day at light intensity of about 700 to about 900 μmoles μmoles m$^{-1}$ s$^{-1}$ and a temperature of from about 78° F. to about 82° F. and about 14 hours of night at a temperature of from about 66° F. to about 70° F.

The method further comprises returning the plant to long day growing conditions as described above.

The method further comprise the step of performing transcriptional profiling from a tissue harvested from the plant grown in step b) and c) to identify yield genes. The yield genes comprise genes that are involved in induction of early flowering, pod set, retention of flowers and pods, and abscission of flowers and pods.

Various cultivars of soybean can be used cultivar for identifying yield genes. Plants are first grown under long day growing conditions as described above until the plants reach V2-V3 stage. Then plants are transferred to short day growing conditions as described above. Plants are sampled at one, three and five days after the experimental plants are transferred to short day growing conditions. Fully-expanded leaves as source leaves and shoot apices are suitable tissue for identifying differentially expressed genes under experimental and control conditions. The tissue sampling is done at the V3 stage. The samples are immediately frozen in liquid nitrogen and stored at −80° C. prior to RNA extraction for transcription profiling.

For identifying genes that are involved in retention of flowers and pods, and/or abscission of flowers and pods, soybean plants were grown as above. After flowering and right before sampling, half the plants are treated with short day conditions to facilitate abscission of their flowers and pods. Plants are sampled at two, four and six days after the transfer to short day conditions and nine hours after light come on. Fully-expanded leaves from a side branch as source leaves and top leaves of the branch as sink leaves and newly opened flower buds prior to and post pollination are suitable tissues for identifying differentially expressed genes under experimental and control conditions. The samples are immediately frozen in liquid nitrogen and stored at −80° C. prior to RNA extraction for transcription profiling.

Several means can be utilized to identify differentially expressed genes in experimental and control plants and are well known to those skilled in the art. These include serial analysis of gene expression (SAGE, SuperSAGE) and gene expression profiling. In one aspect of the invention, gene expression or transcriptional profiling is used to identify yield genes by comparing their differential expression under experimental and control conditions.

RNA is extracted from the pooled samples using a pre-manufactured kit and protocol by OmegaBiotek. A custom made soybean genome expression microarray chip from Affymetrix is used. The microarray contains 1.4 million features (each 11 micron in size) covering 83 thousand genes and some negative alien sequences per array. RNA is checked for quality by estimating OD at 260/280 ratio using nano-drop8000 and quality of 28s/18s ribosome bands using Agilent Bioanalyzer2000. Three hundred nanogram RNA per sample was used in RT/IVT amplification and labeling procedure as provided by InVitrogen and Epicentre. Labeled cRNA probe is fragmented and hybridized to the array. The hybridization, washing, detection, and scanning are done according to Affymetrix protocol.

Analysis is done by Robust Multi Array (RMA) algorithms to perform background correction, global normalization and summarization of intensity data adjusted using the 75$^{th}$ percentile. The intensity data is converted to log base2 prior to the statistical analysis, which uses ANOVA models to analyze the data set and perform the comparisons between data set from experimental and control samples. Differentially expressed genes are identified by using a threshold with a false discovery rate of 5%, a raw probability coefficient of 0.0001 and a 1.5 fold change or greater as the standard for significance. FunCat analysis is used to identify over-representation of functional categories based on molecular, biochemical and cellular characteristics of the proteins encoded by the transcripts. K-means cluster analysis is used to group genes based on similarities of expression profiles, systems network building, and promoter motif analysis.

In another embodiment, the method of the present invention further comprises growing the short day plant under conditions that restricts vegetative growth and enhances flowering. Such conditions comprise growing the short day plant in a soil volume of about 2.0 mL to about 4.0 mL per seed to be produced.

In another embodiment, the method of the present invention further comprises providing the short day plant nutrients sufficient to support seed development. Such nutrients may be selected from the group consisting of Calcium Nitrate, Phosphate, micronutrients, and Magnesium Sulfate wherein the amount of nutrients supplied provides a soil EC of from about 1.0 to about 1.6 mmhos and a soil pH of from about 5.1 to about 6.0.

EXAMPLES

Example 1

This example describes a method for manipulating vegetative and flowering responses in soybean, a short day plant, with external signals for decreasing or increasing seed yield and manipulating seed generation time.

Soybean seeds were sown as one seed per 200 mL pot (McConkey Company, Sumner, Wash.) loosely filled with the Sunshine LP5 soil (Sun Gro Horticulture, Vancouver, BC, Canada) and allowed to germinate and grow under long day conditions in a Green House (GH) or a growth chamber.

The final potting soil was prepared by mixing 3.8 cu.ft. bales of Sunshine #1 soil (Sun Gro Horticulture, Vancouver, BC, Canada) manually or in Gleason batch soil mixer (Hummert International, Earth City, Mo., USA). Eighty mL of APEX® micronutrients and 1000 mL of APEX® 14-14-14 (J. R. Simplot Company, Lathrop, Calif., USA) controlled release fertilizer was added to each bale of soil. Mixed soil was transferred to desired pot sizes. A Saturated Media Extraction test was performed on the mixed soil. The pots filled with mixed soil were watered with Reverse Osmosis water to saturate the soil and until water started to leach. Electro-Conductivity (EC) and pH measurements were taken on the leached water using an EC and pH meter (MYRON L COMPANY, Carlsbad, Calif., USA) such that the EC was in the range of 3.5 to 7 mS and pH was in the range of 5.2-5.7. If the EC was higher than 7, then soil was continually flushed with Reverse Osmosis water until the EC was below 7.

The long day growing conditions were as follows. A photoperiod of 16-18 hours was provided using supplemental lighting to accumulate between 40-60 moles of total light per day. The temperatures were set based on the season and the weather to ensure target temperatures such that to accumulate as many hours per day at or above 86° F. to maximize photosynthesis and minimize night respiration with cooler temperatures. The target temperatures for the cool season were: day, 86° F.-90° F. and night, 68° F.-70° F. and the warm season were: day, 84° F.-88° F. and night, 66° F.-68° F. The ambient $CO_2$ and humidity was maintained below 65%.

A constant and low concentration of nutrient solution and optimal moisture content was also provided to the plants. The plants were irrigated from 1 to 6 times a day depending upon the climate and the pot size. The pots were fertilized with a nutrient solution having a composition and characteristics shown in Table 1.

The short day growing conditions were applied in a growth chamber (GC) e.g., PGR15, PGC20 or GR144 (Conviron, Controlled Environments Inc., Pembina, N. Dak., USA) as follows. Soybean plants at a suitable V stage (e.g., V1 to V4; see Table 2, column 2) were transferred to the GC. Briefly, V1 stage is when first set of tri foliate leaves are unfolded, V2 stage is when the first trifoliate leaf is fully expanded, and V3 is when the second trifoliate leaf is fully expanded. A V-stage is a good measure of physiological stage but vigor must also be used to determine the correct stage. A V3 plant with low vigor may be equivalent to a V2 plant with good vigor. Plants seeded on the same day usually have different development rates. For example, A3525 control take 11 days after seeding to reach V2 and some R1 transgenic seeds may take 21 days to reach V2 stage. The plants were grown at a photoperiod of 10 hours at light intensity of 700-900 μmoles/m/s and temperature of 78-82° F. and 14 hours of night at a temperature of 66-68° F. The plants were irrigated with a nutrient solution (Table 1) in order to provide optimal growth conditions depending upon the size of the plant and the weather conditions. Each plant was grown at a plant density of 0.18 sq. ft. in the GC. The plants were kept in the GC from about 3 to 21 days depending upon the yield needed (see Table 2, column 3).

After subjecting the plants to short day growing conditions, the plants were returned to the long day growing conditions provided in the green house (GH) as described above. The plants were first transplanted to larger pots depending upon the yield needed (Table 2, column 4). The pots were prepared as described above. Maximum pot densities in the GH were dependent upon the pot size and were as follows: 200 mL pot/0.5 sq. ft.; 750 mL pot/1 sq. ft.; 2.7 L pot/2 sq. ft.; and 8.6 L pot/4 sq. ft.

As shown in Table 2, whereas the current short day method yielded only 200 seeds in 120 days, the method of present invention yielded anywhere from 90 seeds to 4000 seeds in 80 to 170 days depending upon the short day induction stage, short day induction period, pot size, and long day period after flowering.

TABLE 1

Composition and characteristics of the nutrient solution used in the present invention. Macro (NPK) and Micro (Rest) nutrients are in ppm.

| pH | EC | Alkalinity | |
| --- | --- | --- | --- |
| 5.2-5.6 | 1.2-1.6 | 3.86 | |
| Ca | Mg | Na | |
| 124 | 48.2 | 2.93 | |
| Cl | B | Fe | Mn |
| 3.05 | 0.326 | 1.44 | 0.136 |
| Cu | Zn | Mo | Al |
| 0.036 | 0.099 | 0.024 | 0.079 |
| NO3-N | NH4-N | Total N | |
| 104 | 12.1 | 116 | |
| S | P | K | |
| 102 | 26.5 | 131 | |

TABLE 2

Manipulation of seed yield in soybean using the method of the present invention.

| | Induction Name 1 | Induction Stage 2 | SD Induction period (days) 3 | Pot Size 4 | Seed Yield 5 | Generation Time (days) 6 | Pot Density/ sq ft 7 | Seeds/ Sq ft 8 |
| --- | --- | --- | --- | --- | --- | --- | --- | --- |
| 1 | Super Rapid Cycle | V1 | 21 | 300 mL | 90 | 80 | 0.67 | 134 |
| 2 | Rapid Cycle | V2 | 14 | 750 mL | 250 | 90 | 1 | 250 |
| 3 | Regular Induction | V2-4 | 14 | 2.7 L | 500 | 120 | 2 | 250 |
| 4 | Super Plant | V2-4 | 7 | 8 L | 2000 | 150 | 5 | 400 |
| 5 | Super Plant Plus | V2-4 | 7 | 10 L | 4000 | 170 | 8 | 500 |
| 6 | Current Short Day Method | V6 | 80 | 8 L | 200 | 120 | 1 | 200 |

Example 2

This example demonstrates extension of the methods described herein to cotton plants.

Short day cotton has an indeterminate vegetative growth habit under long day growth conditions and normally produces very little seed with high amounts of vegetative growth. However, Applicants believe that a high seed yielding cotton plant can be produced by applying the methods of the present invention to a short day cotton variety. Cotton seeds will be germinated under long day conditions and seedlings will be subjected to short day induction conditions for 5 and 10 days at the first and third unifoliate stages to trigger early flowering. Seedlings will then be subjected to long day conditions. The same variations of experimental conditions as described in Example 1 including long day growth conditions, short day induction conditions, light intensity, soil types, temperature, pot size and nutrients will be applied on the cotton plants to produce a high yielding phenotype.

Example 3

This example demonstrates a method of the invention using transcriptional profiling to identifying potential genes conferring increased yield in short day plants.

To identify genes involved in floral initiation, pod initiation, flower set, and pod set, soybean plants of cultivar A3555 are grown in 200 ml pots under long day growing conditions (17 hours of daylight) until the plants reach V2-V3 stage and all the plants are transplanted into 4 L pots. Half the plants are then transferred to short day conditions (10 hours of daylight) for 7 days at 26° C. during the day, 19° C. at night at a light intensity of about 800 μE. Control plants continue to grow under long day growth conditions. Plants are sampled at one, three and five days after the experimental plants are transferred to short day conditions. Plants are sampled one hour and nine hours after lights come on. Fully-expanded second trifoliate leaves on the fourth node are collected as source leaves and pooled. For apex tissue, meristem tissue and non-expanded primordial leaf are collected and pooled. The tissue sampling is done at the V3 stage. The samples are immediately frozen in liquid nitrogen and stored at −80° C. prior to RNA extraction for transcription profiling.

To identify genes that are involved in retention of flowers and pods, and/or abscission of flowers and pods, soybean plants of cultivar A3555 are grown in 200 ml pots under long day growing conditions (17 hours of daylight) until the plants reach V2-V3 stage. Plants are then transplanted into 4 L pots grown under short day conditions (10 hours of daylight) for 7 days at 26° C. during the day at a light intensity of about 800 μE, and at 19° C. at night. After short day conditions, plants are transferred to long day conditions. After flowering and right before sampling, half the plants are treated with short day conditions to facilitate abscission of their flowers and pods. Plants are sampled at two, four and six days after the transfer to short day conditions and nine hours after light come on. Fully-expanded leaves from a side branch between the fourth node and internode are collected as source leaves and pooled whereas top leaves of the branch are collected as sink leaves and pooled. Newly opened flower buds two days prior to and one day post pollination are collected from the entire plant and pooled. The samples are immediately frozen in liquid nitrogen and stored at −80° C. prior to RNA extraction for transcription profiling.

RNA is extracted from the pooled samples using a pre-manufactured kit and protocol by OmegaBiotek. A custom made soybean genome expression microarray chip from Affymetrix is used. The microarray contains 1.4 million features (each 11 micron in size) covering 83 thousand genes and some negative alien sequences per array. RNA is checked for quality by estimating OD at 260/280 ratio using nano-drop8000 and quality of 28s/18s ribosome bands using Agilent Bioanalyzer2000. Three hundred nanogram RNA per sample was used in RT/IVT amplification and labeling procedure as provided by InVitrogen and Epicentre. Labeled cRNA probe is fragmented and hybridized to the array. The hybridization, washing, detection, and scanning are done according to Affymetrix protocol.

Analysis is done by Robust Multi Array (RMA) algorithms to perform background correction, global normalization and summarization of intensity data adjusted using the 75$^{th}$ percentile. The intensity data is converted to log base2 prior to the statistical analysis, which uses ANOVA models to analyze the data set and perform the comparisons between data set from experimental and control samples. Differentially expressed genes are identified by using a threshold with a false discovery rate of 5%, a raw probability coefficient of 0.0001 and a 1.5 fold change or greater as the standard for significance. FunCat analysis is used to identify over-representation of functional categories based on molecular, biochemical and cellular characteristics of the proteins encoded by the transcripts. K-means cluster analysis is used to group genes based on similarities of expression profiles, systems network building, and promoter motif analysis.

All of the materials and methods disclosed and claimed herein can be made and used without undue experimentation as instructed by the above disclosure. Although the materials and methods of this invention have been described in terms of preferred embodiments and illustrative examples, it will be apparent to those of skill in the art that variations can be applied to the materials and methods described herein without departing from the concept, spirit and scope of the invention. All such similar substitutes and modifications apparent to those skilled in the art are deemed to be within the spirit, scope and concept of the invention as defined by the appended claims.

What is claimed is:

1. A method for manipulating seed yield of a short day plant, the method comprising:
   (i) planting a seed of a short day plant and growing the plant under long day growing conditions comprising at least about 14 uninterrupted hours of light per day at a light intensity from about 1000 to about 2000 μmoles m$^{-2}$s$^{-1}$ until the plant has reached a growth stage of about V1 to V4;
   (ii) after the plant has reached a growth stage of about V1 to V4, growing the plant under short day growing conditions for about 3 to about 21 days;
   (iii) after growing the plant under short day growing conditions for about 3 to about 21 days, growing the plant under said long day growing conditions; and
   (iv) allowing seed to form, wherein more of said seed forms relative to a control plant grown for the same amount of time but without all of said steps (i)-(iii).

2. The method of claim 1, wherein the short day plant is selected from the group consisting of soybean, cotton, rice, sugarcane, tobacco, and strawberry.

3. The method of claim 1, wherein the long day growing conditions comprise at least about 14 hours of light per day at a light intensity from about 1000 to about 2000 μmoles m$^{-2}$s$^{-1}$ and a temperature from about 84° F. to about 90° F. and a night temperature from about 62° F. to about 70° F.

4. The method of claim 1, wherein the short day growing conditions comprise maintaining about 9 to about 11 hours of light per day at a light intensity from about 700 to about 900 μmoles m$^{-2}$s$^{-1}$ and a temperature from about 78° F. to about 82° F. and about 14 hours of night at a temperature from about 66° F. to about 70° F.

5. The method of claim 1, further comprising growing at least one short day plant under conditions that restrict vegetative growth and enhance flowering.

6. The method of claim 5, wherein the method further comprises growing the at least one short day plant in a soil volume from about 2.0 mL to about 4.0 mL of soil volume for every seed to be produced.

7. The method of claim 1, further comprising providing the short day plant nutrients sufficient to support seed development.

8. The method of claim 7, wherein the nutrients are selected from the group consisting of Calcium Nitrate, Phosphate, micronutrients, and Magnesium Sulfate and the amount of nutrients supplied provide a soil electro-conductivity (EC) of about 1.0 to about 1.6 mmhos and a soil pH of about 5.1 to about 6.0.

9. A method for manipulating seed yield of a soybean plant, the method comprising:

(i) planting a seed of a soybean plant and growing the plant under long day growing conditions comprising at least about 14 uninterrupted hours of light per day at a light intensity from about 1000 to about 2000 µmoles $m^{-2}s^{-1}$ until the plant has reached a growth stage of about V1 to V4;

(ii) after the soybean plant has reached a growth stage of about V1 to V4, growing the plant under short day growing conditions for about 3 to about 21 days;

(iii) after growing the soybean plant under short day growing conditions for about 3 to about 21 days, growing the soybean plant under said long day growing conditions; and (iv) allowing seed to form on the plant, wherein more of said seed is formed than a control soybean plant grown for the same amount of time but without all of said steps (i)-(iii).

10. The method of claim 9, wherein the long day growing conditions comprise at least about 14 hours of light per day at a light intensity from about 1000 to about 2000 µmoles $m^{-2}s^{-1}$ and a temperature from about 84° F. to about 88° F. and a night temperature from about 62° F. to about 68° F.

11. The method of claim 9, wherein the short day growing conditions comprise maintaining about 9 to about 11 hours of light per day at a light intensity from about 700 to about 900 µmoles $m^{-2}s^{-1}$ and a temperature from about 78° F. to about 82° F. and about 14 hours of night at a temperature from about 66° F. to about 70° F.

12. The method of claim 9, further comprising growing the soybean plant under conditions that restrict vegetative growth and enhance flowering.

13. The method of claim 12, wherein the method further comprises growing the soybean plant in a soil volume from about 2.0 mL to about 4.0 mL of soil volume for every seed to be produced.

14. The method of claim 9, further comprising providing the soybean plant nutrients for supporting seed development.

15. The method of claim 14, wherein the nutrients are selected from the group consisting of Calcium Nitrate, Phosphate, micronutrients, and Magnesium Sulfate and the nutrients are supplied in amounts sufficient to provide a soil electro-conductivity (EC) from about 1.0 to about 1.6 mmhos and a soil pH of about 5.1 to about 6.0.

16. A method for identifying genes conferring increased seed yield in a short day plant, the method comprising:

(i) planting a seed of a short day plant and growing the plant under long day growing conditions comprising at least about 14 uninterrupted hours of light per day at a light intensity from about 1000 to about 2000 µmoles $m^{-2}s^{-1}$ until the plant has reached a growth stage of about V1 to V4;

(ii) after the plant has reached a growth stage of about V1 to V4, growing it under short day growing conditions for about 3 to about 21 days;

(iii) after growing the plant under short day growing conditions for about 3 to about 21 days, growing the plant under said long day growing conditions;

harvesting tissue from the short day plant; and performing transcriptional profiling on the harvested tissue to identify genes that may confer increased seed yield in the short day plant.

17. The method of claim 16, wherein the short day plant is selected from the group consisting of soybean, cotton, rice, sugarcane, tobacco, and strawberry.

18. The method of claim 16, wherein the long day growing conditions comprise at least about 14 hours of light per day at a light intensity from about 1000 to about 2000 µmoles $m^{-2}s^{-1}$ and a temperature from about 84° F. to about 90° F. and a night temperature from about 62° F. to about 70° F.

19. The method of claim 16, wherein the short day growing conditions comprise maintaining about 9 to about 11 hours of light per day at a light intensity from about 700 to about 900 µmoles $m^{-2}s^{-1}$ and a temperature from about 78° F. to about 82° F. and about 14 hours of night at a temperature from about 66° F. to about 70° F.

20. The method of claim 16, further comprising growing at least one short day plant under conditions that restrict vegetative growth and enhance flowering.

21. The method of claim 16, wherein the method further comprises growing the at least one short day plant in a soil volume from about 2.0 mL to about 4.0 mL of soil volume for every seed to be produced.

22. The method of claim 16, further comprising providing the short day plant nutrients sufficient to support seed development.

23. The method of claim 22, wherein the nutrients are selected from the group consisting of Calcium Nitrate, Phosphate, micronutrients, and Magnesium Sulfate and the amount of nutrients supplied provide a soil electro-conductivity (EC) of about 1.0 to about 1.6 mmhos and a soil pH of about 5.1 to about 6.0.

24. The method of claim 16, wherein the genes conferring increased yield on the short day plant comprise genes inducing early flowering, pod set, retention of flowers and pods, or abscission of flowers and pods.

\* \* \* \* \*